US010864066B2

(12) United States Patent
Lee

(10) Patent No.: US 10,864,066 B2
(45) Date of Patent: Dec. 15, 2020

(54) ROTATING ELECTRIC TOOTHBRUSH

(71) Applicant: Dong Chul Lee, Daejeon (KR)

(72) Inventor: Dong Chul Lee, Daejeon (KR)

( * ) Notice: Subject to any disclaimer, the term of this patent is extended or adjusted under 35 U.S.C. 154(b) by 879 days.

(21) Appl. No.: 14/787,175

(22) PCT Filed: Apr. 24, 2014

(86) PCT No.: PCT/KR2014/003588
§ 371 (c)(1),
(2) Date: Oct. 26, 2015

(87) PCT Pub. No.: WO2014/175674
PCT Pub. Date: Oct. 30, 2014

(65) Prior Publication Data
US 2016/0100923 A1 Apr. 14, 2016

(30) Foreign Application Priority Data

Apr. 24, 2013 (KR) .................. 10-2013-0045159

(51) Int. Cl.
*A61C 17/34* (2006.01)
*A46B 9/06* (2006.01)
(Continued)

(52) U.S. Cl.
CPC ............ *A61C 17/3418* (2013.01); *A46B 7/10* (2013.01); *A46B 9/06* (2013.01); *A46B 13/001* (2013.01);
(Continued)

(58) Field of Classification Search
CPC .. A46B 9/04; A46B 9/005; A46B 9/06; A46B 15/0081; A46B 7/10; A46B 9/065;
(Continued)

(56) References Cited

U.S. PATENT DOCUMENTS 2,435,421 A * 2/1948 Blair ...................... A61C 17/26
15/23
2,960,712 A * 11/1960 Hayer .................... A61C 17/00
15/179
(Continued)

FOREIGN PATENT DOCUMENTS

KR 20-0291813 Y1 10/2002
KR 20-0374520 Y1 1/2005
(Continued)

*Primary Examiner* — Mark Spisich
(74) *Attorney, Agent, or Firm* — Rabin & Berdo, P.C.

(57) ABSTRACT

The present invention relates to a rotating electric toothbrush comprising: a main body having a receiving space formed therein, a driving means received in the interior of the main body and providing a rotational force, a toothbrush handle having one end detachably coupled to the driving means, and receiving a rotational force of the driving means to be rotated, a support means coupled to the outer peripheral surface of the other end of the toothbrush handle and having plate-shaped support bodies made of a ductile material and radially formed to be spaced apart from each other, and a plurality of toothbrush bristles implanted between the support bodies. The present invention has a structure in which the toothbrush bristles are radially implanted on the outer peripheral surface of the end of the cylindrical rotating toothbrush handle, thereby removing food leftovers sandwiched on a tooth surface or at an interdental gap without damage of gums, and more surely removing dental plaque from the tooth surface due to silicon bristles implanted between the toothbrush bristles. Further, the silicon bristles implanted between the toothbrush bristles support the toothbrush bristles, thereby preventing deformation of the toothbrush bristles, and a space for receiving toothpaste is formed between the silicon bristles, thereby preventing the toothpaste from easily slipping off. Further, a tongue cleaner, (Continued)

which is detachable and made of a silicon material, is further comprised, thereby easily cleaning a tongue.

4 Claims, 5 Drawing Sheets

(51) Int. Cl.
| | | |
|---|---|---|
| *A61C 17/26* | (2006.01) | |
| *A46B 13/00* | (2006.01) | |
| *A61H 13/00* | (2006.01) | |
| *A46B 7/10* | (2006.01) | |
| *A61B 17/24* | (2006.01) | |
| *A46B 15/00* | (2006.01) | |

(52) U.S. Cl.
CPC ........ *A46B 13/005* (2013.01); *A46B 15/0075* (2013.01); *A61B 17/244* (2013.01); *A61C 17/26* (2013.01); *A61C 17/3472* (2013.01); *A61H 13/00* (2013.01); *A61C 17/3445* (2013.01)

(58) Field of Classification Search
CPC ..... A46B 13/00; A46B 13/001; A46B 13/005; A46B 13/02; A46B 13/023; A46B 15/0075; A61C 17/222; A61C 17/24; A61C 17/26; A61C 17/32; A61C 17/34; A61C 17/3409; A61C 17/3418; A61C 17/3445; A61C 17/3472; A61H 13/00
USPC .................. 15/22.1, 167.1, 160, 23; 601/142
See application file for complete search history.

(56) References Cited

U.S. PATENT DOCUMENTS

| | | | | |
|---|---|---|---|---|
| 3,451,086 | A * | 6/1969 | Burgett | A61C 17/26 15/23 |
| 3,661,018 | A * | 5/1972 | Keefer | A46B 13/023 74/22 R |
| 4,397,055 | A * | 8/1983 | Cuchiara | A61C 17/26 15/22.1 |
| 8,032,967 | B2 * | 10/2011 | Jimenez | A61C 17/349 15/110 |
| 2003/0033680 | A1 * | 2/2003 | Davies | A46B 9/06 15/22.1 |
| 2003/0115699 | A1 * | 6/2003 | Wagstaff | A46B 15/0055 15/111 |

FOREIGN PATENT DOCUMENTS

| | | |
|---|---|---|
| KR | 20-0427125 Y1 | 9/2006 |
| KR | 10-2010-0122494 A | 11/2010 |

* cited by examiner

Prior Art

ROTATING ELECTRIC TOOTHBRUSH

TECHNICAL FIELD

The present invention relates to a rotating electric toothbrush, and in particular to a rotating electric toothbrush wherein laminar silicon bristles are planted into between toothbrush bristles which are planted spaced apart in a radial shape on an outer circumferential surface of an end portion of a cylindrical toothbrush shaft, whereupon any food debris on a tooth surface and stuck between teeth can be efficiently removed without damaging gum with rotating toothbrush bristles, and a dental plague on a tooth surface can be effectively removed with the aid of the rotating silicon bristles.

BACKGROUND ART

As one of tooth brushing methods recommended by the dental clinics, there is a method wherein teeth are brushed by an effective roll technique. This method might not be well performed due to muscular structures of persons' hands and arms. Instead of this roll technique, a scrub method in general is used, wherein tooth brushings are performed leftward and rightward.

If the scrub method is used for a long time, cervical abrasion or hypersensitive teeth diseases may easily occur, and any food debris may be pushed into between teeth, which may result in the deposition of dental plague, thus causing a periodontal disease.

For the above mentioned reasons, an electric toothbrush is widely used so as to keep teeth clean and healthy, wherein a toothbrush head with a number of planted toothbrush bristles is rotated with the aid of an operational characteristic of such an electric motor.

FIG. 1 is a schematic view illustrating a conventional electric toothbrush, wherein teeth can be brushed in such a way to rotate the toothbrush head 200 wherein a plurality of toothbrush bristles 200a are planted, with the aid of the driving of the electric motor disposed in the inside of the electric toothbrush 100. The use of which is easier than an ordinary toothbrush, so ordinary adults as well as kids who are not good at brushing may be motivated to think it as a good tool in terms of the caring of teeth. Old men and women who may feel unnatural when using arms can easily brush teeth without providing any special training to them. For this reason, the use of such an electric toothbrush is increasing.

Since the conventional electric toothbrush 100 is configured in such a way that the toothbrush head 200 can rotate parallel with the surface of each tooth, the surface of each tooth can be brushed clean with the aid of the toothbrush bristles 200a planted into the toothbrush head, but it still is not easy to remove any food debris stuck between the teeth. In addition, it takes long to finish tooth brushing since the contact surface area between the toothbrush bristles 200a planted into the toothbrush head 200 and the teeth is not large.

In addition, the toothbrush bristles may be over bent when in use due to the characteristics of the electric toothbrush which rotates at a high speed by the electric motor, whereupon the toothbrush bristles may be easily deformed or damaged, so toothpaste on the toothbrush bristles may easily run down.

DISCLOSURE OF INVENTION

Accordingly, the present invention is made in an effort to resolve the above mentioned problems. It is an object of the present invention to provide a rotating electric toothbrush wherein laminar silicon bristles are planted into between toothbrush bristles which are planted spaced apart in a radial shape on an outer circumferential surface of an end portion of a cylindrical toothbrush shaft.

It is another object of the present invention to provide a rotating electric toothbrush wherein silicon bristles are planted in such a way to form a space in an outward direction at a circumference at an end of a toothbrush shaft, the space being configured to receive toothpaste.

It is further another object of the present invention to provide a rotating electric toothbrush which may equip with a detachable tongue cleaner made of a silicon material.

Technical Solution

To achieve the above objects, there is provided a rotating electric toothbrush, which may include, but is not limited to, a main body which includes a receiving space in the inside of the main body; a driving unit which is received in the inside of the main body and is configured to supply torque; a toothbrush shaft one end portion of which is engaged detachable to the driving unit, the toothbrush shaft being configured to rotate by receiving the torque from the driving unit; a support unit which is secured to an outer circumference of the other end of the toothbrush shaft, the support unit including a laminar support body made of an elastic material in such a way to be spaced apart from each other in a radial direction; and a plurality of toothbrush bristles which are planted into between the support bodies.

In addition, the support body each may include a first support bristle and a second support bristle which is spaced apart by a predetermined distance from the first support bristle, wherein a space is formed between the first support bristle the second support bristle to receive toothpaste.

In addition, the support unit further includes a ring engaging unit which is installed surrounding the toothbrush shaft, and the support body extends integral in an outward direction, and the toothbrush bristles are planted into the ring engaging unit.

In addition, the first and second support bristles each include a laminar support bristle body, and a tapered portion is formed at a front end of the support bristle main body.

In addition, the driving unit is configured to simultaneously provide torque and a straight reciprocation movement force.

There is further provided a mode changing unit which is configured to change the driving mode of the driving unit. It is preferred that the driving mode may include any of a speed changing mode which is configured to change the speed of the driving unit, a rotation mode configured in such a way that the driving unit can provide torque, a straight reciprocation mode which is configured in such a way that the driving unit can provide a straight reciprocation movement force, and a mixed mode which is configured in such a way that the driving unit can simultaneously provide torque and the straight reciprocation movement force.

It is preferred that there is further provided a tongue cleaner which is engaged detachable to the driving unit and is made of a silicon material.

Advantageous Effects

According to the present invention, a gum may not hurt thanks to a configuration wherein toothbrush bristles are planted in a radial shape on an outer circumference at an end of a cylindrical rotating toothbrush shaft, and any food debris on a tooth surface and stuck between teeth can be effectively removed, and a plague on a tooth surface can be effectively removed with the aid of silicon bristles planted between toothbrush bristles.

Since the silicon bristles planted between the toothbrush bristles may support the toothbrush bristles, any deformation of the toothbrush bristles can be prevented, and since a space configured to receive toothpaste is formed between the silicon bristles, the toothpaste can be prevented from easily rolling down.

Since a detachable tongue cleaner made of a silicon material is further provided, it is easy to clean tongue.

MODES FOR CARRYING OUT THE INVENTION

Figure 1:
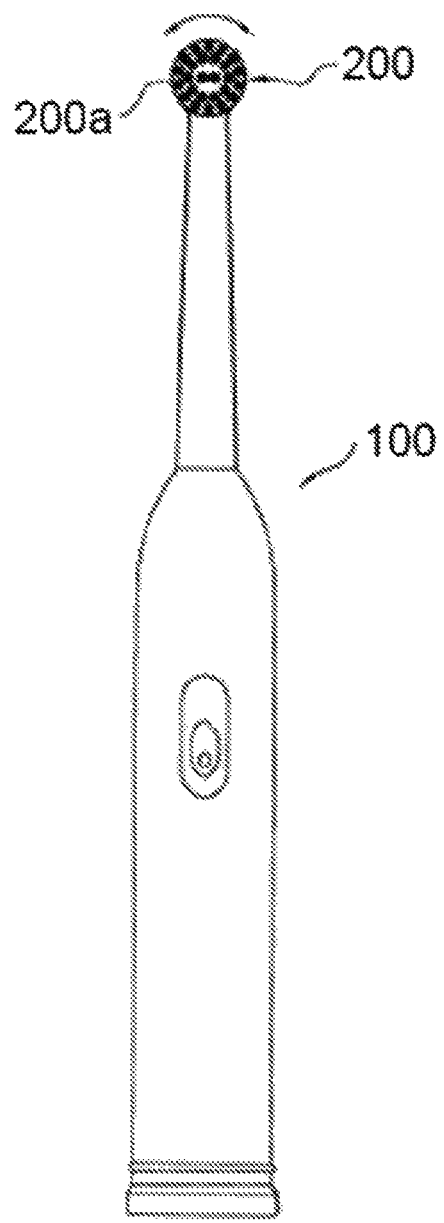
FIG. 1 is a schematic view illustrating a conventional electric toothbrush.

The present invention will be described herein below in detail with reference to the drawings. In the drawings, it is noted that the same components will be given the same reference numbers in anywhere throughout the descriptions, and known functions and configuration which might make unclear the subject matters of the present invention will be omitted from descriptions.

Figure 2:
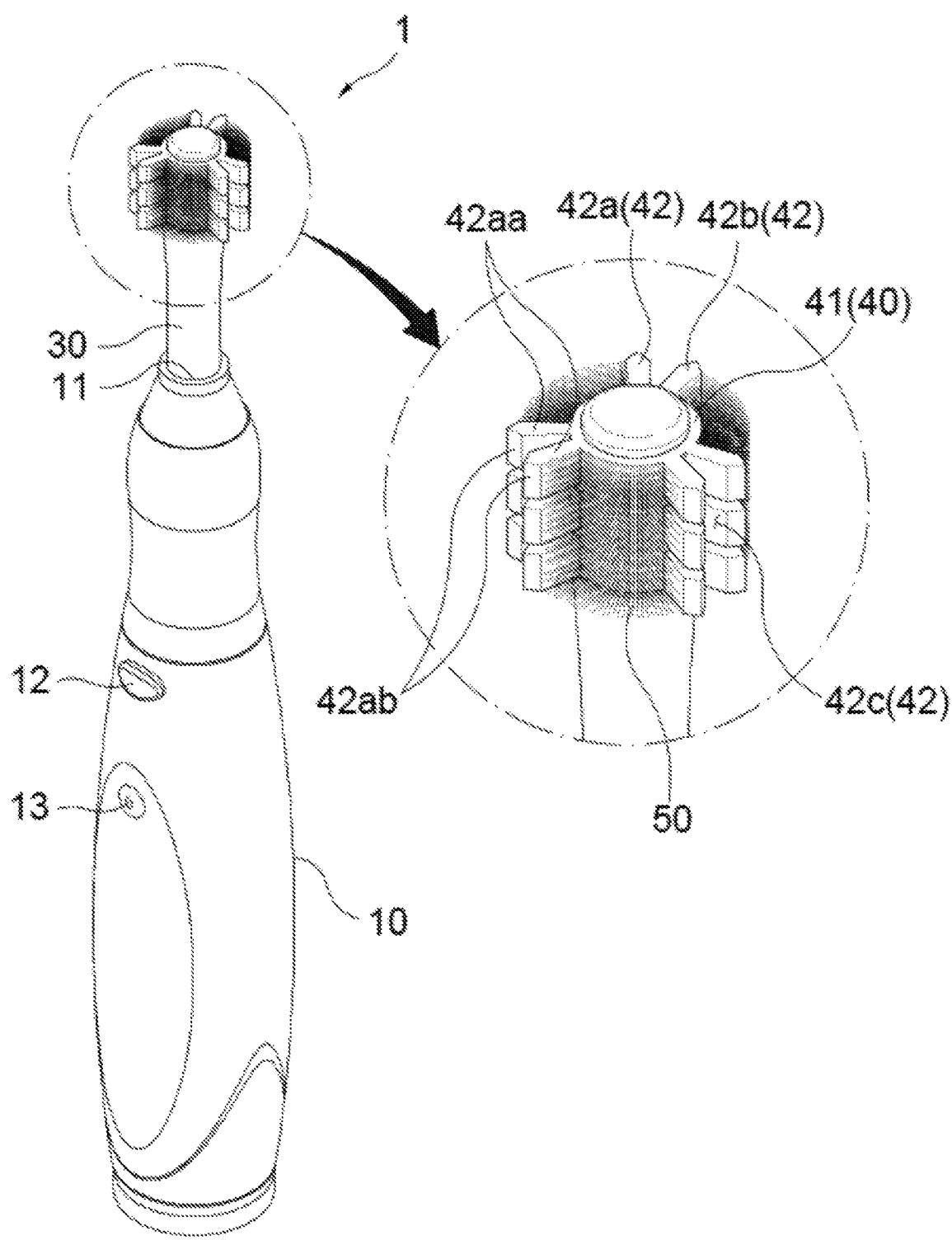
FIG. 2 is a perspective view illustrating a rotating electric toothbrush according to the present invention.
Figure 3:
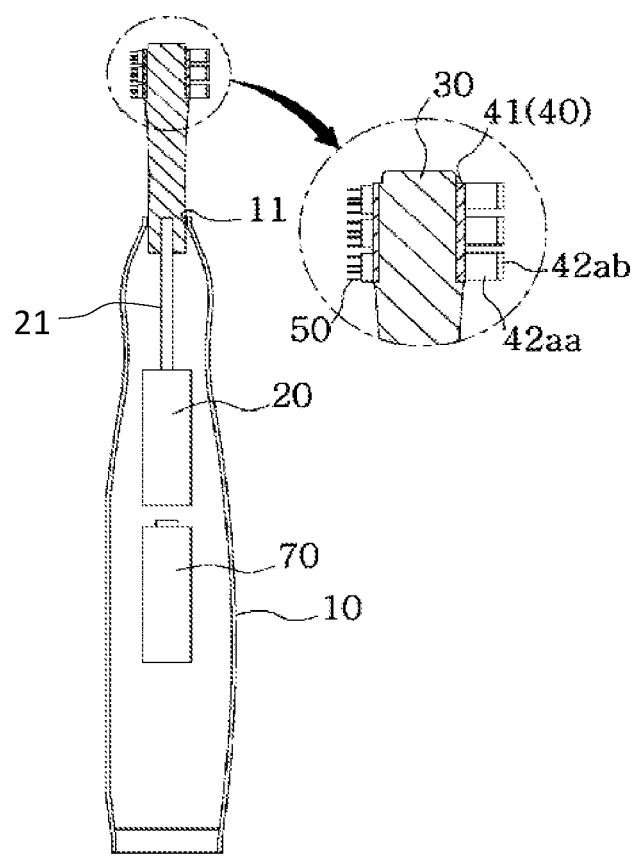
FIG. 3 is a cross sectional view illustrating a rotating electric toothbrush according to the present invention.

FIG. 2 is a perspective view illustrating a rotating electric toothbrush according to the present invention. FIG. 3 is a cross sectional view illustrating a rotating electric toothbrush according to the present invention.

Referring to FIGS. 2 and 3, the rotating electric toothbrush 1 according to the present invention may include, but is not limited to, a main body 10, a driving unit 20, a toothbrush shaft 30, a support unit 40, and toothbrush bristles 50.

The main body 10 may equip with a receiving space in the inside thereof, an insertion groove 11 formed on the top thereof, and a power switch 12 disposed at one side of the outer circumference so as to supply electric power to the driving unit 20.

The driving unit 20 and a battery 70 for supplying electric power to the driving unit 20 may fit into the receiving space of the main body.

The battery 70 may be an ordinary battery or may be a chargeable battery. In case where the chargeable battery is used, any of a wireless charging method and a USB terminal-base charging method may be used.

The driving unit 20 is disposed in the receiving space formed in the inside of the main body 10 and may be formed of an ordinary motor which is able to supply torque to the toothbrush shaft 30 which is engaged to an end of the driving unit. As an embodiment, a driving shaft 21 may be coupled to the driving means and rotated by the torque of the driving means along with the toothbrush shaft 30.

The driving unit 20 may separately include a mode changing unit 13 at one side of the outer circumference of the main body 10 so as to change the driving mode.

Such a driving move may be a speed changing mode which is configured to adjust the speed of the driving unit 20 and which may be categorized into a low speed rotation mode, a normal rotation mode and a high speed rotation mode. The speed changing mode can be changed whenever the mode changing unit 13 is pressed.

In this way, the driving unit 20 may allow to adjust the rotation speed with the aid of the speed changing mode, more specifically, kids or weak and old users who have weak teeth may use the low speed rotation mode, and adults may use the normal rotation mode, and when it needs to clean tongue by engaging a tongue cleaner, which will be described later, the user may selectively use the high speed rotation mode, whereupon it is possible for a user to select and use an appropriate mode that the user wants.

The toothbrush shaft 30 is made in a circular bar shape one end of which is inserted through the insertion groove 11 on the top of the main body 10 and is detachably engaged to the driving unit 20.

The support unit 40 may include, but is not limited to, a ring engaging unit 41 which is made of an elastic material and is installed covering an outer circumference at the other end of the toothbrush shaft 30; and a plurality of support bodies 42 which are made of a laminar elastic material and are formed integral with the ring engaging unit 41 and extend outward of the ring engaging unit 4l in a radial direction at regularly spaced-apart intervals, the support bodies 42 being made of elastic materials.

Here, it is preferred that the support unit may be made of a silicon or an elastic synthetic resin material.

In addition, each support body 42 may include a plurality of first support bristles 42a, and a plurality of second support bristles 42b. Since the first support bristles 42a and the second support bristles 42b are formed spaced-apart in a radial direction at regular intervals, a toothpaste receiving part 42c may be formed between the first support bristles 42a and the second support bristles 42b, thus preventing toothpaste from rolling down during tooth brushing.

In addition, the first and second support bristles 42a and 42b each may include a laminar support bristle main body 42aa, and a tapered part 42ab which is inclined from both sides of the front end of the support bristle main body 42aa toward the center of the front end, whereupon if the toothbrush shaft 30 rotates, the front ends of the first and second support bristles 42a and 42b may linearly contact with the surface of each tooth, while downwardly brushing the surface of each tooth, which may consequently result in a perfect removal of the plague deposited on the surface of each tooth.

The toothbrush bristles 50 may consist of ordinary toothbrush bristles which in general are used in a typical toothbrush and may be planted into between the support bodies 42 formed of the first and second support bristles 42a and 42b. If the toothbrush shaft 30 rotates, it is possible to remove any food debris on the surface of each tooth or stuck between the teeth.

It is preferred that such toothbrush bristles 50 are made of fine bristles so as to easily remove any food debris stuck between the teeth.

In this way, since the toothbrush bristles 50 are planted into between the support bodies 42 which each consist of the first and second support bristles 42a and 42b, and both sides are supported by the support bodies 42, the toothbrush bristles 50 may not be over bent even at a high speed rotation, thus preventing any deformation of the toothbrush bristles 50.

The rotating electric toothbrush 1 according to the present invention may be made of a silicon material and may further include a tongue cleaner which is engaged detachable to an end portion of the driving unit 20. After tooth brushing is finished, the toothbrush shaft 30 is separated, and then the tongue cleaner is engaged, thus easily cleaning the tongue.

Figure 4:
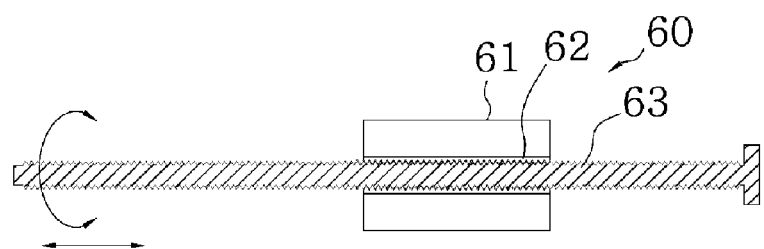
FIG. 4 is a cross sectional view illustrating a driving unit of a rotating electric toothbrush according to another exemplary embodiment of the present invention.

FIG. 4 is a cross sectional view illustrating a driving unit of a rotating electric toothbrush according to another exemplary embodiment of the present invention.

Referring to FIG. 4, the driving unit 20 of the rotating electric toothbrush 1 according to another exemplary embodiment of the present invention may be a linear DC motor 60 which may include, but is not limited to a motor main body 61, a motor bushing 62 which is installed passing through the motor main body 61, and a motor shaft 63 which fits into the motor bushing 62.

In the liner DC motor 60, since male threads are formed on an outer circumference of the motor shaft 63, and female threads matching with the male threads are formed on an inner circumference of the motor bushing 62 to which the motor shaft 63 is engaged, a straight reciprocation movement in forward and backward directions can be performed while the motor shaft 63 alternately rotates in normal and reverse directions.

If the above linear DC motor 60 is used as a driving unit 20 of the rotating electric toothbrush 1 according to the present invention, the toothbrush shaft 30 engaged to the motor shaft 63 may perform a straight reciprocation movement while performing a rotational movement, whereupon foam generation power of the toothpaste can be enhanced during tooth brushing, which may result in enhanced tooth brushing efficiency.

Figure 5:
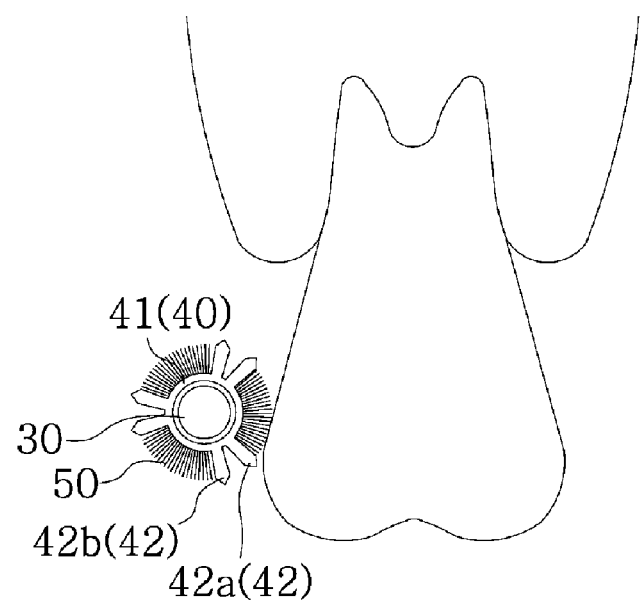
FIG. 5 is a schematic view illustrating a state where toothbrush bristles of a rotating electric toothbrush contact with the surface of each tooth according to the present invention.
Figure 6:
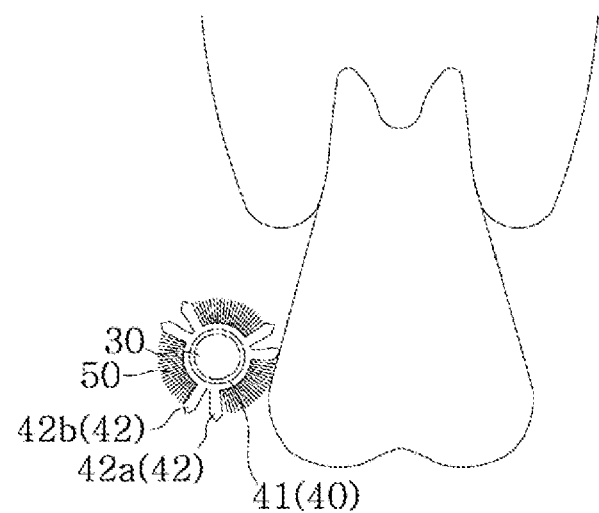
FIG. 6 is a schematic view illustrating a state where a support body of a rotating electric toothbrush contacts with the surface of each tooth according to the present invention.

FIG. 5 is a schematic view illustrating a state where toothbrush bristles of a rotating electric toothbrush contact with the surface of each tooth according to the present invention. FIG. 6 is a schematic view illustrating a state where a support body of a rotating electric toothbrush contacts with the surface of each tooth according to the present invention.

If the user supplies electric power to the driving unit 20 through the power switch 12, torque of the driving unit 20 is transferred to the toothbrush shaft 30, and since the toothbrush shaft 30 which has received the torque will rotate, the support unit 40 engaged to an end portion of the toothbrush shaft 30 and the toothbrush bristles 50 planted into the ring engaging unit 41 of the support unit 40 rotate together, thus brushing the surface of each tooth.

As illustrated in FIGS. 5 and 6, when the toothbrush bristles 50 contact with the surface of each tooth as the toothbrush shaft 30 rotates, the toothbrush bristles 50 formed of fine bristles may allow to remove any food debris on the surface of each tooth and stuck between the teeth, and since the support body 42 formed of the first support bristles 42a and the second support bristles 42b contacts with the surface of each tooth, the front ends of the first and second support bristles 42a and 42b which are formed tapered can closely contact with the surface of each tooth, thus downwardly brushing the surface of each tooth, which may surely remove any plague which has been deposited on the surface of each tooth.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

The invention claimed is:

1. A rotating electric toothbrush, comprising:
a main body having a receiving space thereinside;
a driving means disposed in the receiving space of the main body and configured to supply torque;
a driving shaft rotating by the torque of the driving means, wherein a first end of the driving shaft is coupled with the driving means;
a toothbrush shaft arranged in a straight line with the driving shaft, wherein a first end portion of the toothbrush shaft is detachably coupled with a second end of the driving shaft, whereby the toothbrush shaft is configured to rotate along with the driving shaft by the torque from the driving means; and
a support means secured to an outer circumference of a second end portion of the toothbrush shaft and including a plurality of support bodies formed made of an elastic material, wherein each of the support bodies includes a first support bristle and a second support bristle, the first support bristle and the second support bristle being formed by a laminar support bristle body extending along the axis of the toothbrush shaft and also extending in a radial direction and spaced apart from each other by a predetermined distance such that a first space is formed between the first support bristle and the second support bristle,
wherein a second space is formed between a first support body and a second support body,
no toothbrush bristle is planted in the first space, and
a plurality of toothbrush bristles are planted in the second space,
wherein the support means further includes a ring engaging unit surrounding the toothbrush shaft.

2. The toothbrush of claim 1, wherein a tapered portion is formed at a front end of the laminar support bristle body.

3. The toothbrush of claim 1, wherein the driving means further provides a straight reciprocation movement force.

4. The toothbrush of claim 1, further comprising:
a mode changing switch configured to change a speed of the driving means by changing the driving mode of the driving means.

* * * * *